US009739768B2

(12) United States Patent
Russell et al.

(10) Patent No.: US 9,739,768 B2
(45) Date of Patent: *Aug. 22, 2017

(54) METHODS AND REAGENTS FOR IMPROVED SELECTION OF BIOLOGICAL MATERIALS

(71) Applicant: Russell Biotech, Inc., Doylestown, PA (US)

(72) Inventors: Thomas R. Russell, Huntington Valley, PA (US); Pauline McGann, Miami Beach, FL (US); Mike Musick, Mason, OH (US); Michael Ciocci, Royersford, PA (US)

(73) Assignee: Russell Biotech, Inc., Doylestown, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/882,841

(22) Filed: Oct. 14, 2015

(65) Prior Publication Data
US 2017/0067886 A1 Mar. 9, 2017

Related U.S. Application Data

(62) Division of application No. 10/208,939, filed on Jul. 31, 2002, now Pat. No. 9,435,799.

(51) Int. Cl.
*G01N 33/553* (2006.01)
*G01N 33/577* (2006.01)
*G01N 33/543* (2006.01)

(52) U.S. Cl.
CPC ... *G01N 33/5434* (2013.01); *G01N 33/54326* (2013.01); *G01N 33/54346* (2013.01);
(Continued)

(58) Field of Classification Search
CPC ......... G01N 33/5434; G01N 33/54326; G01N 33/553; G01N 33/577; G01N 33/54346; G01N 33/54353
See application file for complete search history.

(56) References Cited

U.S. PATENT DOCUMENTS 5,536,644 A * 7/1996 Ullman .................... B03C 1/01
209/214
6,132,955 A * 10/2000 Talley .................... C12Q 1/001
204/400

(Continued)

*Primary Examiner* — Gail R Gabel
(74) *Attorney, Agent, or Firm* — Joseph F. Aceto, Esq.

(57) ABSTRACT

Methods, apparatus and compositions for separating a desired or undesired population or subpopulation from a biological sample are disclosed herein. The selection procedure is based on ferromagnetic, dense particles in a preferred size range from about 0.8 to about 1.2 microns. Specific binding agents are bound to the particles that recognize and bind to specific molecules on the targeted population or subpopulation, and the particles are mixed with the sample in such a way as to promote movement of the particles relative to the sample, promoting binding to the targeted population or subpopulation without non-specifically binding to non-targeted populations in the sample. Because of the large particle density, the bound population is separated from the fluid sample by gravity. Alternatively, the sample, including the bound, targeted population, is placed in a magnetic field such that the particles separate from the sample by evenly distributing over the vessel wall thus limiting non-specific trapping of the non-targeted population.

12 Claims, 8 Drawing Sheets

(52) U.S. Cl.
CPC ..... *G01N 33/54353* (2013.01); *G01N 33/553* (2013.01); *G01N 33/577* (2013.01); *G01N 2440/32* (2013.01)

(56) References Cited

U.S. PATENT DOCUMENTS

| | | | |
|---|---|---|---|
| 6,623,982 B1* | 9/2003 | Liberti | G01N 33/54326 |
| | | | 435/7.1 |
| 2003/0040129 A1* | 2/2003 | Shah | B01L 3/5027 |
| | | | 506/32 |
| 2006/0003371 A1* | 1/2006 | Russell | G01N 33/5434 |
| | | | 435/6.15 |

* cited by examiner

METHODS AND REAGENTS FOR IMPROVED SELECTION OF BIOLOGICAL MATERIALS

RELATED APPLICATION

This application is a divisional application of U.S. application Ser. No. 10/208,939 which was filed Jul. 31, 2002, now issued U.S. Pat. No. 9,435,799, which is hereby incorporated in its entirety.

BACKGROUND OF THE INVENTION

Field of the Invention

This invention generally relates to novel particles which are particularly useful for research, diagnostic and therapeutic applications for human and animal health care in the field of cell selection. More specifically the invention relates to novel ferromagnetic dense particles (FDP), and methods of preparation and use thereof, in applications that include selection of cells, cell components, bacteria, viruses, toxins, nucleic acids, hormones, proteins, receptor-ligand complexes, other complex molecules or any combination thereof. The particles can in addition have application in molecular biology and protein purification protocols Background Art The enhancement, via positive selection or depletion, of a population or subpopulation of cells or cellular-like material in fluid from a human or animal subject can be utilized for a number of applications. For instance in the area of cell therapy, the depletion of tumor cells prior to an autologous stem cell transplant or the depletion of certain immune cells prior to an allogeneic stem cell transplant can prove beneficial to the patient. In diagnostics, the enrichment of rare cells may be useful for early diagnosis of metastatic disease (see for example U.S. Pat. No. 6,365,362; April 2002; Terstappen, L. et al.). In the research arena, both positive and negative selection procedures are powerful tools for cell-based studies and, in the molecular biology arena, selection tools that permit the detection of specific genes or mRNA's are extremely important for both gene discovery and as research tools.

Conventional cell enrichment/depletion and other selection technologies are based on either gradient centrifugation procedures well known in the art or solid-phase microparticles (herein used interchangeably with particles) that are linked to binding agents, which separate cells via magnetic attraction or gravity. Microparticles can range in diameter from about 50 nm to about 50 microns and can have either smooth or raged surfaces. Magnetic selection technologies include colloidal superparamagnetic particles (see, for example, those provided by Immunicon Corporation or Miltenyl Biotech) and micron sized particles (such as those provided by Dynal Corporation). Gravity selection technology can include micron size dense particles (HDM), such as those provided by Eliglx, a subsidiary of Blotransplant, Inc. Magnetic Selection:

As is well known in the art, several types of magnetic particles can be prepared, including but not limited to, superparamagnetic and ferromagnetic. U.S. Pat. Nos. 5,411,863 and 5,466,574 (May 1995; Miltenyl, S. and November 1995; Liberti, P. et al., respectively) teach that superparamagnetic particles are the particle of choice for biological selection applications. Superparamagnetic materials have in recent years become the backbone of magnetic selection technology in a variety of health care and blo-processing applications. Superparamagnetic materials are highly magnetically susceptible—i.e. they become strongly magnetic when placed in a magnetic field but rapidly lose their magnetism when the magnetic field is removed. This property makes it easy to isolate cell populations and to resuspend the cells when the magnetic field is removed. Superparamagnetism occurs in ferromagnetic materials when the crystal diameter is decreased to less than a critical value. Such materials, regardless of their diameter (about 25 nm to about 100 microns) have the property that they are only magnetic when placed in a magnetic field. The basis for superparamagnetic behavior is that such materials contain magnetic material in size units below about 20 to 25 nm, which is estimated to be below the size of a magnetic domain. A magnetic domain is the smallest volume for a permanent magnetic dipole to exist. Ferromagnetic materials, on the other hand, are strongly susceptible to magnetic fields and are capable of retaining magnetic properties when the field is removed. Ferromagnetism occurs only when unpaired electrons in the material are contained in a crystalline lattice thus permitting coupling of the unpaired electrons. The prior art teaches that ferromagnetic particles with permanent magnetization have considerable disadvantages (see for example U.S. Pat. No. 5,411,863; May 1995; Miltenyl, S. and U.S. Pat. No. 5,466,574; November 1995; Liberti, P. et al.) for applications in biological material selection, since suspensions of these particles easily aggregate following exposure to a magnetic field due to their high magnetic attraction for each other. For this reason ferromagnetic particles have not been used in the art for biological (cell selection/nucleic acid) applications.

Gravity Selection:

Solid phase microparticles that separate targeted from non-targeted populations on the basis of gravity rather than magnetics have been described (for example, U.S. Pat. No. 5,576,185; November 1996; Coulter, W. et al. and Zwerner, et al. J. Imm. Methods (1997) 14:31-34). Currently, particles that are separated based on gravity are relatively dense and large with diameters between the range of approximately 3 to 10 microns. A known feature of these particles is that because of the density difference between particles and cells, end-over-end mixing allows the particles to pass through a substantial portion of the fluid sample. The particles traverse past the cells of Interest and in doing so bind to the targeted cell population without non-specifically binding to non-target cells. This leads to an efficient separation and a high recovery of non-targeted cells. The separation and recovery of non-targeted cells is superior to that found with superparamagnetic selection alone. These dense particles are designed to settle by gravity both as a mixing manner (discussed above) and as a manner to separate the desired population of cells from the remainder of the cell suspension. In fact, previous descriptions (for example U.S. Pat. No. 5,576,185; November 1996; Coulter, W. et al.) teach away from the use of smaller particles in gravity selection. For example, the disclosure of this patent teaches that superparamagnetic particles are intended to be maintained in suspension in the sample and consequently are designed for very slow or substantial elimination of gravity settling in the sample suspension. Typically, well-coated materials below 150 nm will show no evidence of settling for as long as 6 months and even longer (see U.S. Pat. No. 5,622,831; April 1997; Liberti, P. et al.). Thus, superparamagnetic particles are not applicable in gravity selection technology or density difference mixing. Both procedures function optimally at a density difference of at least 2-3 fold between the particles and the target biomaterial when capturing cells and settling by gravity.

Gravity separation addresses several drawbacks inherent in magnetic separation procedures that utilize superparamagnetic particles including non-specific cell loss due to trapping, time of magnetic collection when using colloidal particles, and/or the high magnetic gradients required for collection of colloidal particles. When using superparamagnetic colloidal particles, there often is not sufficient magnetic force to hold the targeted cells at the wall of the chamber. This leads to contamination of the non-targeted cells with targeted cells. Also, sample preprocessing is often required (i.e. removal of red blood cells via density gradients before addition of superparamagnetic particles). However, by using gravity selection, sample preprocessing can often be eliminated and minimal cell loss of non-target cells occurs, but a drawback of the conventional art has been that due to the size of the particles and the nature of gravity mixing, cells with low antigen density are not easily isolated, thus limiting its utility.

Accordingly, it would be desirable to have an effective method of depleting or selecting one or more populations of cells or cell-like material without affecting the remaining populations in the sample, over a broad range of antigen density on the cell surface. The method ideally should be inexpensive, fast, result in high yield and not restricted by the sample volume.

SUMMARY OF THE INVENTION

The invention provides improved methods, apparatus, and compositions for the selection of biological materials. This selection consists, in part, of mixing and separating components. Separation defined for the purposes of this invention includes any mechanism dependent upon the physical properties of the particles involved. For example, this would include the particle's density or magnetic properties. Specifically, the invention provides for an Improved selection procedure based on the properties of sufficiently dense particles. These particles, when coupled to an appropriate binding agent offer a unique advantage over prior art because of their superior magnetic properties and negligible carry-over compared to superparamagnetic particles. These same particles are able to separate by gravity, similar to larger particles, but offer the advantage of not limiting their selection to high density targets.

The method embodying the invention herein disclosed can be utilized with a variety of reactions involving binding agents and their corresponding recognition sites. As utilized herein, cells are defined as animal or plant cells, including cellular bacteria, fungi, which are identifiable separately or in aggregates, and including cell-like material, which appears like or is substantially similar in physical properties to the foregoing. Cells are the least structural aggregate of living matter capable of functioning as an independent unit. For example, cells can be human red blood cell (RBC) and white blood cell (WBC) populations, cancer or other abnormal cells from tissue, cells found in bone marrow and/or blood samples. Cells, suitably tagged or labeled, can be expected to operate through the method of this invention.

The term "binding agent" as used herein defines various molecule(s) that detect and react with one or more specific complementary molecule(s). Examples include, but not limited to, the following specific complementary molecular pairs; antibody/antigen, drug/drug receptor, nucleic acid/complementary nucleic acid, lectin/carbohydrate molecule, or hormone/hormone receptor.

In one preferred embodiment of the present invention, it has been found that ferromagnetic dense particles, within a certain diameter size range, can be used to efficiently select specific targeted populations without causing non-specific loss of non-targeted populations. Within a given diameter size range and under desired magnetic conditions, ferromagnetic dense particles are able to function in this manner even though they maintain their magnetic properties upon removal of a magnetic field. Both the method and means provided by the present invention, when performed together with the particles of the invention, are effective for the removal of specific populations of cells and for the positive selection of specific populations. The method, means, and particles of the invention utilize both a mixing manner that takes advantage of the difference in density between the particles and the targeted biomaterial to effectively capture targeted populations, and a separating manner that takes advantage of the magnetic properties of ferromagnetic dense particles to hold rapidly and tightly the targeted populations at the wall of the container, thus permitting effective removal of non-targeted populations without carryover of targeted populations as is seen with colloidal superparamagnetic particles of the prior art.

To accomplish this selection, in a preferred embodiment of the invention, a plurality of ferromagnetic dense particles, having one or more binding agents thereupon, is combined with a fluid sample containing a biomaterial target of interest. The sample is mixed such that the relatively dense particles traverse back and forth past the biomaterials, binding to those targeted by the binding agents. Following mixing, the sample is placed in a magnetic field that promotes even dispersion of the particles along the vessel wall containing the sample. The separation is followed by removal of the remaining sample. The entire process enhances the number of remaining cells of interest in the sample, which were not targeted by the particles. Additionally, the targeted population can be easily resuspended while still bound to the particles (even though the particles are ferromagnetic), washed, and subsequently removed from the particles by ways known in the art. The preferred particle will be in the size range of approximately 0.5 to 2 microns in diameter and made of magnetic material such as, but not limited to nickel, cobalt, or iron.

In a second embodiment of the invention, at least a two-fold density difference between the target biomaterial and particle allows efficient selection. Separation during this selection is based upon gravity allowing the more dense particles to settle out of solution, but could also encompass buoyancy with a less dense particle in the fluid sample. An effect of gravity upon the particles of the invention could also occur through centrifugation procedures known in the art.

The method, means, and particle composition of the invention herein described are effective for the depletion or positive selection of specific populations. Particles with a diameter range of approximately 0.5 microns to a size where gravity selection is inconsistent between low and high antigen densities on target biomaterials. A preferred diameter of between about 0.5 microns to about 1.5 microns will separate more rapidly for selected target populations. The most preferred particle diameter in accordance with the invention is approximately 1 micron for efficient selection of specific target populations without non-specific loss of non-target populations. These particles, when linked to a specific binding agent, will settle by gravity to separate target biomaterials with both a high and low density of recognition sites. Gravity separation forces the particles to collect at the base of the containment vessel, which permits effective removal of non-targeted populations remaining in the fluid sample, but also allows efficient isolation of targeted populations through ways known in the art.

BRIEF DESCRIPTION OF THE DRAWINGS

FIG. 4A shows results prior to ferromagnetic dense particle selection, then after selection with ferromagnetic dense particles containing anti-CD 15 (FIG. 4B) and after selection with ferromagnetic dense particles containing anti-CD45/4 and anti-CD15 (FIG. 4C).

FIG. 5A depicts the profile of an untreated whole blood sample. FIG. 5B shows the profile after 5 min magnetic separation with ferromagnetic dense particles. FIG. 5C shows the resulting profile after a 1 min magnetic separation with ferromagnetic dense particles.

FIG. 6A shows the leukocyte profile of whole blood without selection. FIG. 6B shows the leukocyte profile after selection with large (>3000 nm) magnetic particles linked to anti-CD45. FIG. 6C depicts the result of selection with smaller 1400 nm diameter particles linked to anti-CD45.

DETAILED DESCRIPTION OF THE INVENTION

According to a preferred embodiment, the present invention encompasses methods, apparatus, and particle composition for rapid and efficient selection of target populations or subpopulations in a fluid sample. This selection will recognize both low and high density sites on target biomaterials.

The disclosed invention has particular utility in various laboratory and clinical procedures involving bio-affinity reactions. In such procedures, particles are used which are relatively dense and could be magnetically responsive compared to the targeted biomaterial. Further, the particles constitute a binding agent capable of binding the molecule of interest in the test sample. In the disclosed invention, a particle-target complex is formed between the ferromagnetic dense particle and targeted biomaterial after the binding agent recognizes the target molecule(s). The selection of target population or subpopulation is accomplished through efficient mixing and separation.

Figure 1:
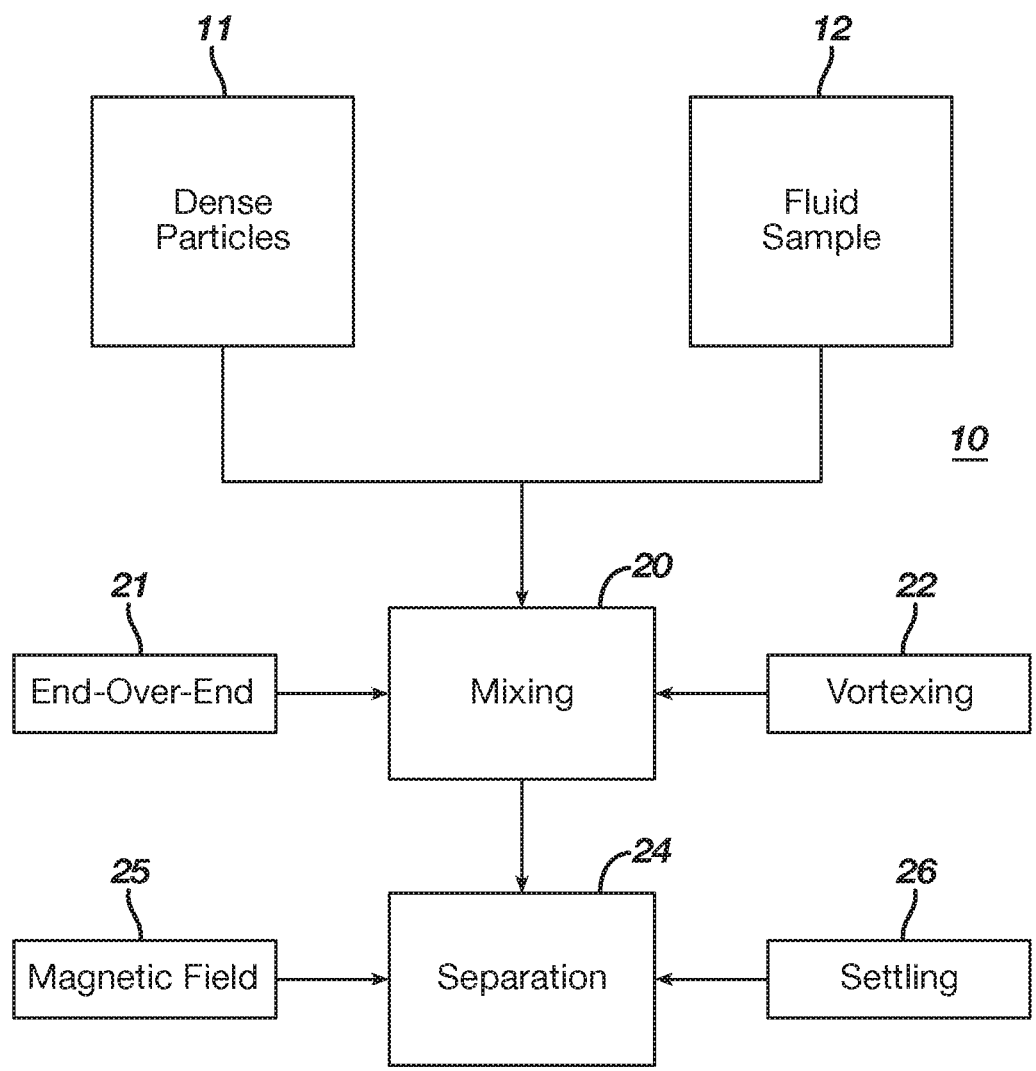
FIG. 1 is a schematic block diagram of the two embodiments of selection with dense particles according to the invention.

As shown in FIG. 1, one embodiment of the method and apparatus according to the invention is depicted in a flow chart (10). The apparatus includes a fluid sample (12) containing a target population as described below. The apparatus (10) also includes a source of dense particles (11) as manufactured and described below. The particles (11) include a binding agent, which is able to bind specifically to a target population. The binding agent is bound to the particles (11) by any method known in the art. The particles (11) are combined with at least a portion of the fluid sample (12) in a mixing stage (20). Depending on the volume, the mixing stage (20) is either end-over-end (21) or vortexing (22). The combination is allowed to form particle-target complexes where, together with any particles not forming complexes, are separated as illustrated by block (24).

Once the particles (11) have been mixed with the fluid sample (12), they are separated by either settling (26) or by movement induced through a magnetic field (25).

The apparatus (10) can be an automatic device to combine the fluid sample (12) and the particles (11), and then move them between the stages. Also, the apparatus (10) can be manual where an operator uses a test tube or similar container through the mixing (20), separating (24), settling (26), or magnetically-Induced movement (25). Finally, the apparatus can be in a semi-automated fashion, using a combination of automated and manual use.

There are two principle embodiments for the methods portion of the invention that differ only in the separation component of the selection process. While both require efficient particle mixing, in a particularly preferred embodiment a magnetic field is utilized to separate targeted material from the fluid sample. A further embodiment utilizes the density difference between an individual particle of the invention and Its target to perform a separation in the fluid sample of non-target components. For example, separation could be the result of a gravitational effect or buoyancy.

Such bio-affinity reactions as described above can be employed in testing biological samples for the determination of a wide range of target biomaterials, representative of which are cells, cell components, cell subpopulations (both eukaryotic and prokaryotic), cell debris, bacteria, parasites, antigens, specific antibodies, specific biological factors, such as vitamins, viruses and specific nucleic acid sequences, as in the case of gene probe analysis. Thus, the methods of the invention can be used to carry out cell selection for the analysis or isolation of cells including, by way of example but not limitation: T-cells; B-cells, CD4 positive cells from leukocytes; lymphocytes from leukocytes; granulocytes from leukocytes; monocytes from leukocytes; tumor cells from normal cells and stem cells from bone marrow or leukopheresis product.

For cell selection, the fluid sample can be, for example, a biological fluid including whole blood or a portion thereof, bone marrow, leukopheresis product, spinal fluid, urine, or other body fluids containing populations or subpopulations, such as described above and as can be conceived by one skilled in the art.

To operate in accordance with a particularly preferred embodiment of the invention, the particle must be ferromagnetic, and should have a density difference of more than two-fold greater than the individual targeted biomaterial to ensure proper mixing. For example, iron, cobalt, nickel (and various alloys of these metals) are typical ferromagnetic dense particles. Ferromagnetic dense particles are metals, which can be permanently magnetized upon application of an external magnetic field. This external field is typically applied by another permanent magnet or electromagnet.

Metallic particles greater than about 30 nm. In diameter typically are considered ferromagnetic. Thus, the lower limit particle size can be in the range of 50 nm in diameter. The upper limit in particle diameter is defined operationally as that particle diameter above which the ferromagnetic dense particles cannot be dispersed by simple mixing after having been placed in a magnetic field. Preferably, this upper limit is in the diameter size range of approximately 2.5 microns. Thus, the particles that are operable in the invention can range in size from approximately 50 nm in diameter to approximately 2,500 nm in diameter with a more preferred diameter in the range of from about 500 nm-to 1,500 nm and a most preferred size range of from about 800 nm-to 1,200 nm (about 0.8-1.2 microns). It will be appreciated that the density of the particle must be sufficiently different than that of the target biomaterial such that the particles traverse past the target population of biomaterial during mixing, thus leading to binding of the target population with little or no non-specific binding of non-targeted populations. It is a specific and advantageous feature of the invention that loss of the non-targeted cell population is minimal, on the order of less than 10%. The density of the particle should be preferably at least two-fold more than the target biomaterial, but not more than about 14 g/cc (blood cells have a density on the order of 1.05 g/cc). The more preferred range of particle density for targeting populations is about 7 g/cc to about 9 g/cc, with the most preferred particle density at approximately 9 g/cc.

According to the present invention, and as will be readily appreciated by those skilled in the art, the volumes of the fluid sample can vary depending on the procedure being performed. For research and diagnostic applications a volume as little as ten microliters can be utilized while for some diagnostic applications and clinical applications the volumes can range from typically around 1 ml up to several liters. A particularly advantageous feature of the invention is that both diluted/processed (centrifugation; gradient centrifugation; gravity) and undiluted samples can be processed. The sample (diluted or undiluted) is simply added to the particles or the particles are added to the sample for applications such as, but not limited to, removal of a subset of leukocytes from undiluted whole blood, or removal of tumor cells or immune cells from leukopheresis products prior to transplantation.

Due to the above described density differences, in the practice of the invention mixing causes the particles to traverse gently past the target population or subpopulation and bind efficiently to recognition sites with little or no non-specific binding to non-targeted populations or subpopulations. This results in a very high yield of non-targeted populations or subpopulations with highly enriched targeted populations or subpopulations. Any mixing process must promote an effective movement of particles past their target population. One such process, but not limited to, is end-over-end mixing. End-over-end mixing is appropriate for volumes greater than 0.5 ml, but can be easily performed for smaller volumes. The mixing vessel can be totally full of liquid, which minimizes sloshing, or the vessel can be partially full which permits sloshing. A test tube holder that rotates end-over-end at speeds from about 5 revolutions per minute to about 30 revolutions per minute is generally preferred. For volumes at least 10 ul, mixing can be accomplished by vortexing or nutation with a preferred volume of about 0.2 to 0.5 ml. Vortexing with larger volumes can be possible as any mixing process that promotes movement of particles relative to a target population falls within the scope of the invention. Mixing times can vary depending on the mixing process. For small volumes, mixing times on the order of seconds to minutes are appropriate; while for larger volumes mixing times range from about 1 to 20 minutes with more preferable mixing being about 1 to about 5 minutes and a most preferred mixing time being with the range of about 4 to 5 minutes. It will be appreciated that mixing times can be outside the preferred range and still fall within the scope of the invention.

Magnets appropriate for capture of targeted cells bound to particles have been described. As an example, see U.S. Pat. No. 5,186,827; February 1993; Liberti, P. et al., the disclosure of which is incorporated herein by reference. In a particularly preferred embodiment of the present invention, the magnetic field generating source can constitute sets of from 2 to 6 permanent magnets or electromagnets. The magnets are arranged so as to define a cavity, which accommodates the container. In this embodiment, the polarity and positioning of the magnets located on the opposite sides of the cavity are such as to produce flux lines, which generate a high gradient magnetic field within the test medium container and expose the sample fluid to the magnetic field. The magnets can be housed in a ferromagnetic yoke, preferably of cylindrical configuration, which serves to enhance the field strength produced by the apparatus. By controlling the quantity of magnetic particles added to the test medium, relative to the exposed surface area of the wall of the container in contact with the test medium and controlling the orientation of such exposed surface, so as to be substantially coextensive with the flux lines of the magnetic field. It is possible to cause the magnetic particles to adhere along the exposed surface of the container wall in essentially a single layer. By operating in this way, occlusion of nonspecifically bound substances, such as non-targeted cells, in the immobilized magnetic particles is virtually negligible. Besides the preferred embodiment discussed above, any magnetic configuration that attracts the particles to the vessel wall without leading to non-specific trapping of non-targeted cells falls within the scope of the invention. Magnetic separation times vary depending on the sample volume and range from approximately around five seconds up to ten minutes. It is to be noted that a significant advantage of the present invention, which utilizes ferromagnetic dense particles, over selection technologies based on superparamagnetic particles, is that very short magnetic capture times are possible. This results in a very rapid selection process.

Though any ferromagnetic dense particle in the desired size range will work in the invention, a particular method for making suitable particles is described below. Methods for making metallic particles are well known in the art (see for example, Kekllklan, et al., *Coll. & Surf. A*, 1994, 92:267-275 and Zach, M. P., Penner, R. M., *Adv. Mat.*, 2000, 12:878). Synthesis of ferromagnetic dense particles containing nickel:

1. Weigh out 4.0 gm sodium hydroxide and dissolve completely in 100 ml beaker by stirring while beaker is covered with parafilm.
2. Weigh out 2.04 gm nickel chloride and dissolve in 100 ml distilled water in a 200 ml beaker.
3. Pour 200 ml distilled water into a clean reaction vessel at room temperature.
4. After nickel chloride solution has mixed for 20 minutes, examine to determine if any debris is floating on the surface of the solution. If debris is present, decant fluid leaving debris behind.
5. Measure out 14 ml triethanolamine. Under a hood, add triethanolamine to the nickel chloride solution. Observe an expected color change to aqua green.
6. Measure 38.5 ml of hydrazine.

7. Add the sodium hydroxide solution to the nickel chloride-triethanolamine solution while continuing stirring on a magnetic stirrer. Observe a color change to a dark pea green color.
8. After complete mixing pour the nickel chloride-triethanolamine solution, through the funnel into a reaction vessel. The reaction vessel contains a lid that has a port for adding materials. The port is capped during the reaction. Also, a condenser is attached to the lid and vented to the outside. The condenser has room temperature water passing through it. The production of particles takes place in a chemical hood.
9. Add measured hydrazine to the reaction vessel. Remove funnel and cap with a plug.
10. Increase heat to 105° C. and stir.
11. Observe reaction vessel to ensure that reaction is not occurring too violently. If foam is rising too high into the condenser add approximately 200 ul of butyl alcohol to reduce foaming.
12. Once the reaction has occurred—at approximately 105° C.—the solution in the reaction vessel will change from green to black.
13. Allow reaction to proceed to completion (around 2.5 hrs).
14. Verify the reaction is complete by checking for the presence of excess hydrazine. Turn off stirrer and determine whether level of foaming rises or not. If level rises resume stirring to speed continue to burn off excess hydrazine. If level does not rise the reaction is complete.
15. When reaction is complete, turn off heat and continue stirring to speed up cooling.
16. Decant supernatant from particles and save for neutralization.
17. Rinse and suspend particles in distilled water.
18. Rinse 6 times.
19. Place final particle pellet in beaker covered with aluminum foil and place in oven at 250° C. for 48 hours.
20. Remove beaker from oven and allow particles to cool.

Figure 2:
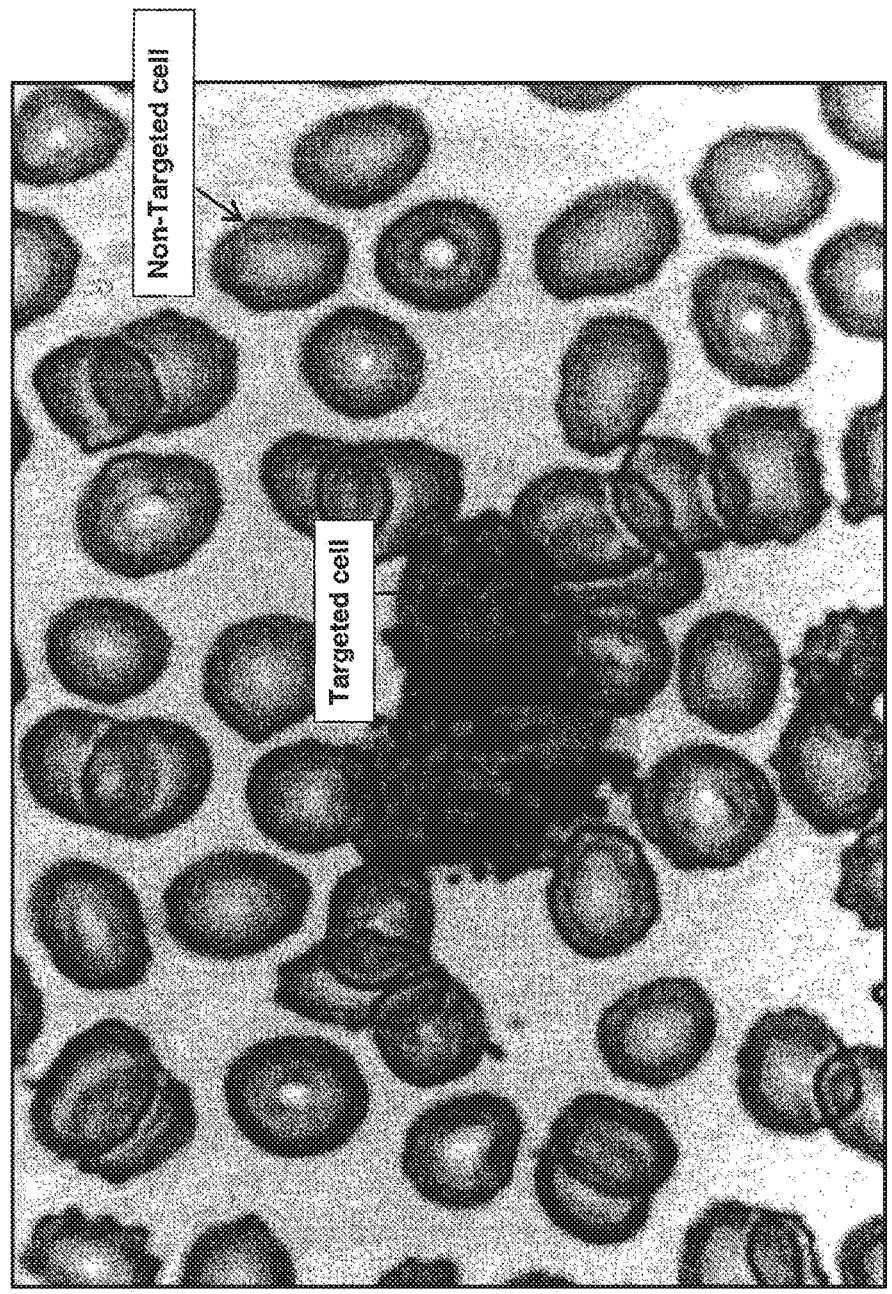
FIG. 2 shows the result as seen by microscopic analysis (400×) from mixing ferromagnetic dense particles with the anti-CD15 antibody bound thereto in blood taken from a patient with breast cancer. Ferromagnetic dense particles are bound to cancer cells (target population), while no binding was observed with non-targeted populations.

Following the above, binding agents such as monoclonal antibodies can then be attached to particles of the invention by methods known in the art such as by adsorption or covalent attachment. A particularly useful particle is one that has goat-anti-mouse (GAM) attached to it. Using particles of the invention, any specific antibody to a desired molecule can be easily attached to GAM. Another convenient approach is the use of a streptavidin particle that can bind specific biotinylated binding agents. FIG. 2 shows the particles of the invention (CD15 FDP) bound to targeted cells, obtained from a blood sample of a breast cancer patient. As shown, no binding of the CD15 FDP was exhibited with the non-targeted red blood cells.

A second embodiment of the invention utilizes the settling ability of the particles of the invention to separate the target population from the fluid sample. Settling for purposes of this invention is defined as a separation of the particles of the invention away from a substantial portion of the fluid sample because of an unequal effect of an Independent or outside force upon the particle-target complex and the rest of the sample. For example, either gravity or the buoyancy of the particles will cause settling from the fluid sample.

Within this embodiment, the particles of the invention also include non-ferromagnetic dense particles. Gravity settling with these particles of the invention allows for the capture of targeted biomaterials having both high and low density recognition sites. Gravity settling by other particles has been described previously (see for example, U.S. Pat. No. 5,576,185; November 1996; Coulter, W. et al.) where selection is limited to higher antigen dense cells within a target population. Surprisingly using the particles of the invention, gravity separation is not limited to high density, antigens on target biomaterials, but has been found to result in a broader, more efficient selection of the targeted population.

Centrifugation, also included as a mode for settling, can be used to separate the particles of the invention following proper mixing. The particles of the invention have an advantage of providing rapid and efficient mixing with relatively low time and speeds of centrifugation for separation of target populations.

As previously mentioned, the method, means, and particles of the invention are particularly suitable for binding and separating targeted populations. Once selected by proper mixing, the targeted populations can be separated from a fluid sample by gravity settling or placement in a magnetic field. With either separation, the remaining sample is enriched with the non-targeted population. If the targeted populations are desired, the remaining sample is removed leaving the targeted population in high yield and purity. The magnetic effect upon the ferromagnetic particle-target complex can then be eliminated by removal of the magnetic field either by mild vortexing or any process of degaussing known in the art capable of disaggregating the particle-target complexes. Finally, the targeted population can be released from the particles again through mild vortexing or by any process known in the art that would release the particle from the particle-target complex. For example, target populations can be released by incubation with mouse IgG when using a GAM particle.

The invention will be more particularly described in the following examples, which are intended to be illustrative of the invention, but in no way limiting of its scope.

EXAMPLE 1

Figure 3A:
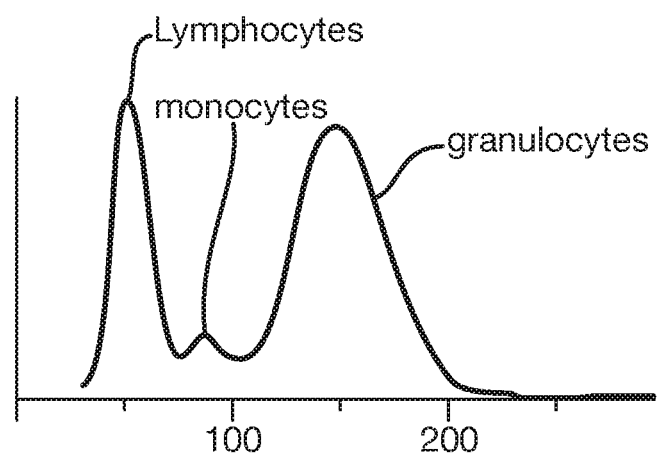
FIG. 3 shows the results of immunomagnetic cell selection of blood analyzed on a hematology analyzer. An untreated blood sample shows granulocytes to be a major subpopulation of leukocytes along with lymphocytes and monocytes (FIG. 3A). Ferromagnetic dense particles containing the anti-CD15 antibody specifically remove targeted granulocytes without loss from the non-targeted cell population (FIG. 3B).
Figure 3B:
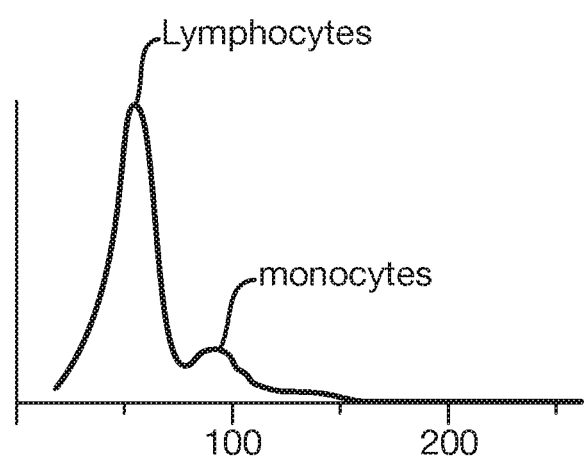
Figure 5A:
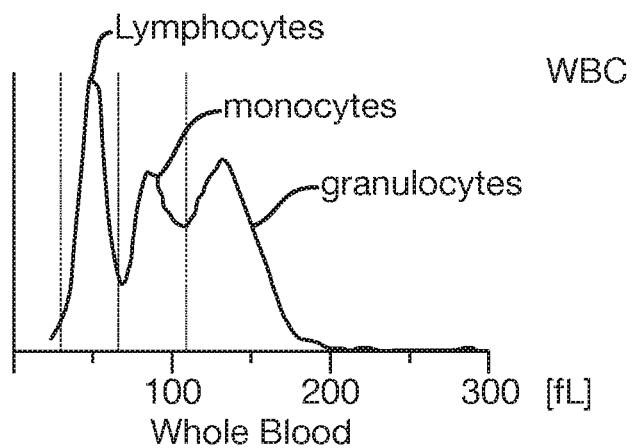
FIGS. 5A, 5B and 5C shows a time course for magnetic separation with ferromagnetic dense particles containing anti-CD45 with whole blood samples using the invention as disclosed.
Figure 5B:
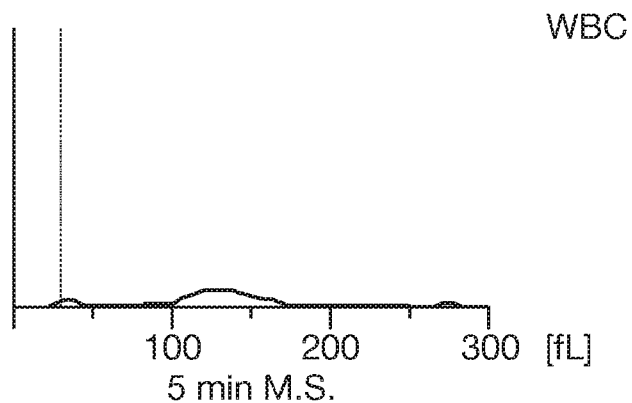

Granulocytes are Efficiently Separated from Whole Blood Using Antibody Labeled Ferromagnetic Dense Particles of the Invention CD15 is present on the majority (>99%) of granulocytes, a major subpopulation of leukocytes. Anti-CD15-nickel particles were used to test the specific selection of targeted cells and the effect of the particles on removal of non-targeted cells non-specifically. Nickel particles were labeled with an anti-CD15 monoclonal antibody (Beckman Coulter, Miami, Fla.) by adsorption. 100 ul of a 20% wt/volume of CD15-nickel particles were added to one ml whole blood in a 12×75 mm glass test tube. The sample was mixed end-over-end at 30 rpm for five minutes and then immediately separated by placement in a magnet for another five minutes. The supernatant was removed and analyzed on a hematology analyzer (Sysmex KX-21, Roche Diagnostics Corp.) for depletion of granulocytes. FIG. 3A demonstrates the three major subpopulations (lymphocytes, monocytes and granulocytes) that make up the white blood cell (leukocyte) population in whole blood. FIG. 5B demonstrates the effective selection of granulocytes from the sample with CD15-nickel particles. The lymphocyte count ($1.6 \times 10^3$ cells/ul before selection vs $2 \times 10^3$ cells/ul after selection) and red blood cell count ($4.8 \times 10^6$/ul before and after selection) did not change, showing that non-targeted cells were not selected non-specifically.

EXAMPLE 2

Figures 4A, 4B, 4C:
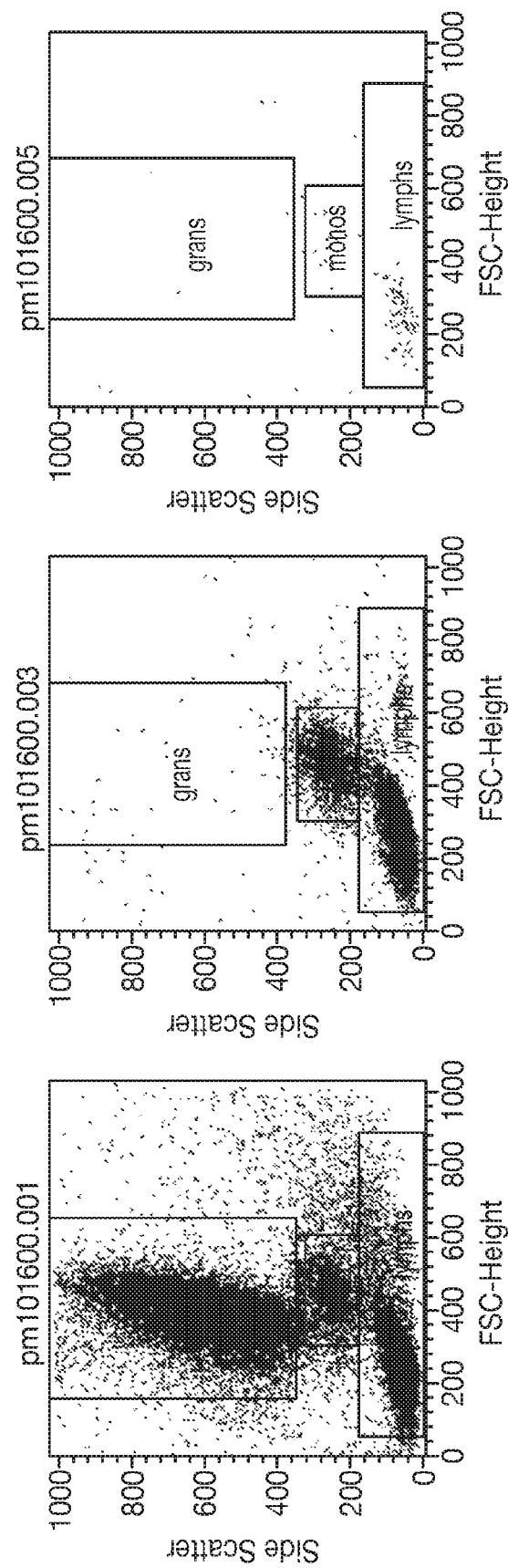
FIGS. 4A, 4B and 4C shows the results of flowcytometric analysis of blood samples.

Leukocyte Populations and Subpopulations are Selected Using Multiple Binding Agents Specific to Different Molecules Ferromagnetic dense particles of the present invention can be used with one antibody bound to the particle or multiple antibodies bound to a single particle in order to effectively select all populations of interest. In this example CD15-ferromagnetic dense particles (one ml whole blood; mixing end-over-end at 30 rpm for five min; separating for five min in a magnetic field) effectively selected for granulocytes, as shown in Example 1. Again the selection of granulocytes was greater than 99% without any loss in lymphocytes (Table 1; FIG. 4B) compared to control (FIG. 4A), demonstrating the specific selection of target cells without non-specific loss of non-targeted cells. CD15 is expressed on monocytes, but the antigen density per cell is at least a log lower than the antigen density on granulocytes. Thus, CD15 only selected for 17% of the monocytes. In order to improve the selection of monocytes and to select for lymphocytes, a second particle was combined with the CD15-ferromagnetic dense particles. The particle contained CD45 and CD4 on a single particle (CD4 is known to be expressed on monocytes). Following standard mixing/separation conditions (as above for CD15), the combination of a CD15 particle plus a CD45/CD4 particle effectively selected greater than 99% of the leukocytes (Table 1 below, FIG. 4C) in 10 min. FIG. 4A shows the starting populations of lymphocytes, monocytes and granulocytes prior to selection. Analysis was by forward light scatter vs 90 degree light scatter. The analysis was performed on a FACS Calibur (Becton Dickinson).

Surprisingly when mixing times are drastically reduced, granulocyte selection is still complete (FIG. 7). In a 150 ul whole blood sample when mixing times are reduced from 2 minutes to approximately 3 seconds, granulocytes were completely removed with the addition of 50 ul of the CD 15-ferromagnetic dense particles. Also, monocytes in the same samples were not completely, but significantly reduced. Further as shown in the last panel of FIG. 7, granulocytes were again completely removed, but with 1/10 the amount of CD15-ferromagnetic dense particles (CD15-FDP).

TABLE 1

| PERCENT LEUKOCYTE DEPLETION | | | | |
|---|---|---|---|---|
| Particles | Lymphocytes | Monocytes | Granulocytes | Leukocytes |
| CD15 | 0 | 17.5 | 99.1 | 60.6 |
| CD15 + CD45/CD4 | 99.2 | 99.2 | 99.9 | 99.7 |

EXAMPLE 3

Particles of the Invention have a Dramatically Reduced Mixing Time and Magnetic Separation Time Compared with Colloidal Superparamagnetic Particles Colloidal superparamagnetic particles effectively select desired populations but mixing times and magnetic separation times are known in the art to be relatively long because of the superparamagnetic nature of the particles. CD45-superparamagnetic particles were used to select leukocytes from whole blood. According to manufacturer's instructions, mixing time was 15 minutes and magnetic separating time was 15 minutes. Time parameters chosen in Table 2 are above and below the manufacture's values.

TABLE 2

| SELECTION METHOD | PERCENT LEUKOCYTE SELECTION |
|---|---|
| CD45-superparamagnectic particles (30 min) | 92 |
| CD45-superparamagnectic particles (10 min) | 8 |
| CD45-nickel particles (30 min) | 92 |
| CD45-nickel particles (10 min) | 95 |

Figure 5C:
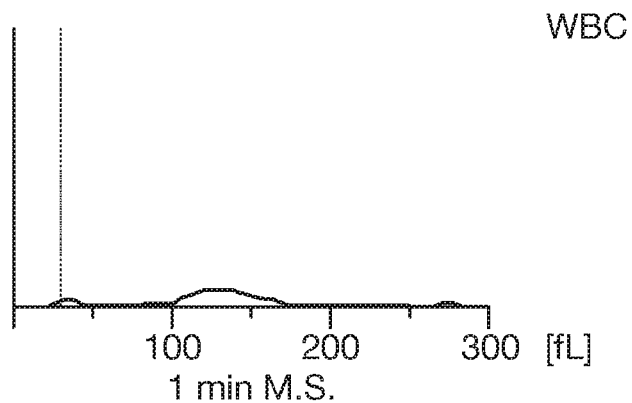

These results (Table 2) show that CD45-superparamagnetic particles effectively select leukocytes but, when the mixing/separation times are decreased below manufacturer's suggested times to ten minutes, selection is not as effective. However, using the particles of the invention, selection is effective both at 30 min and 10 min, a result that was unexpected based on the prior art. The reduced selection times can be attributed to the density and ferromagnetic properties of the nickel particles (Table 2). Further studies revealed that the magnetic separation times during selection are as short as one minute (FIG. 5). FIG. 5A shows the major populations of white blood cells (lymphocytes, monocytes and granulocytes). FIGS. 5B and 5C demonstrate that following end-over-end mixing of 1 ml of whole blood with CD45 nickel particles magnetic separation for five minutes or 1 minute, respectively, is sufficient to select the leukocytes.

EXAMPLE 4

Ferromagnetic Dense Particles have Reduced Magnetic Separation Times when Compared to Multiple Sizes of Superparamagnetic Particles The magnetic separation times of various superparamagnetic particles ranging in diameter from 200 nm to 4500 nm and particles of the invention are listed in Table 3. Particles were diluted in 1 ml phosphate buffered saline and placed into a spectrophotometer cuvette. The cuvette was placed into a modified holder having magnets flanked on each side of the cuvette. As the particles were pulled to the sides of the cuvette by the magnet, light scatter at 600 nm decreased to baseline. The times listed in Table 3 are the times required to reach baseline.

TABLE 3

| PARTICLE | DIAMETER (Nanometers) | MAGNETIC COLLECTION TIME |
|---|---|---|
| DYNAL | 4500 | 20 sec |
| Superparamagnetic particles | 200 | 260 sec |
| Ferromagnetic dense particles (lot #) | | |
| TRB | 1450-2160 | 7 sec |
| PM042001 | 1780-2800 | 5 sec |
| MP050101 | 1250-1800 | 10 sec |
| PM050801 | 1700-2600 | 3 sec |
| PMO50901 | 1600-2400 | 5 sec |

EXAMPLE 5

Ferromagnetic Dense Particles of the Invention are Resuspended Following Exposure to a Magnetic Field Ferromagnetic dense particles (100 ul placed in one ml of phosphate buffered saline) described in the disclosed invention were sized using the Coulter N4 (Beckman Coulter, Miami, Fla.). Following exposure to a magnetic field (either a point source or a quadrupole), a second sample was resuspended by simple inversion while a third sample was resuspended by vortexing. The results in Table 4 demonstrate that simple inversion is not sufficient to disaggregate the particles whereas vortexing does return the particles to their original non-aggregated state. Thus, the magnetic field can be operationally overcome with ferromagnetic dense particles in a manner similar to superparamagnetic particles.

TABLE 4

| Condition | Particle Size |
| --- | --- |
| Pre-magnet | 1720 nm |
| Post magnet-Inversion | 4960 nm |
| Post magnet-Vortexing | 1620 nm |

Larger dense particles such as those disclosed in U.S. Pat. No. 5,786,185; November 1996; Coulter, W. et al. that range in diameter of from about 3-10 microns cannot be readily dispersed once placed in a magnetic field (Table 5). These particles are too large to determine particle diameter using particle sizers known in the art (such as the Coulter N4), but their settling properties can be investigated before and after exposure to a magnetic field. 100 ul of dense particles (INCO 123; 20% wt/volume) was mixed with 1 ml of phosphate buffered saline (PBS) and allowed to settle by gravity. A second tube was exposed to a magnetic field and the magnetic pellet was resuspended by simple inversion while a third tube was placed in a magnetic field and the pellet was resuspended by vortexing. As can be seen in Table 5, ferromagnetic dense particles, having a diameter of about 3 microns or larger, remain magnetized and cannot be dispersed by inversion or vortexing.

TABLE 5

| Condition of Particles | Settling Time |
| --- | --- |
| No magnetic exposure | 90 seconds |
| Post magnet + Inversion | 17 seconds |
| Post magnet + Vortexing | 17 seconds |

EXAMPLE 6

Figure 6A:
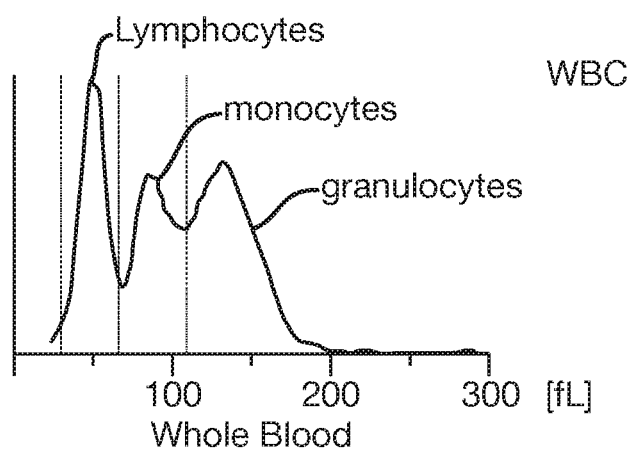
FIGS. 6A, 6B and 6C shows the effect of particle size on the selection of leukocytes in blood samples.
Figure 6B:
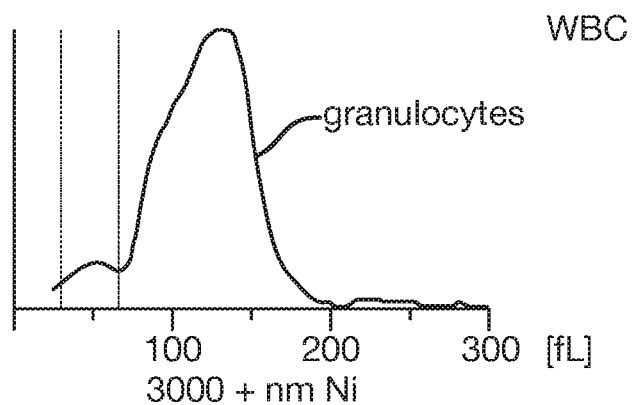
Figure 6C:
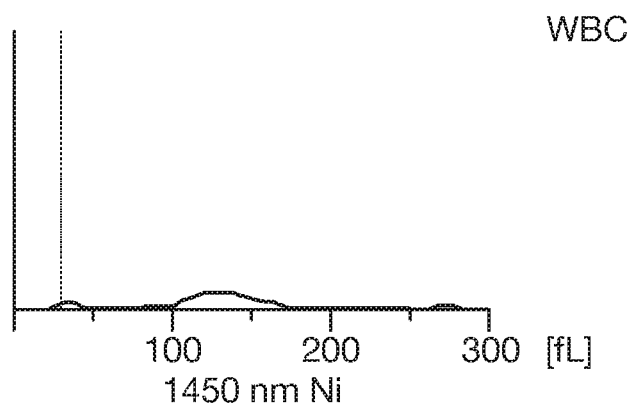

Leukocyte Selection Becomes More Efficient and Less Selective for Antigen-Rich Subpopulations as Ferromagnetic Dense Particle Diameter Decreases Three different particles (>3.5 microns; 2.4 microns and 1.45 microns in diameter) were labeled with anti-CD45, a pan leukocyte marker. Leukocyte selection was performed on 1 ml samples of whole blood in the following manner 100 ul of each particle solution was added to three different glass test tubes (5 ml capacity). The tubes were centrifuged to pellet the particles and the supernatant was removed, 1 ml of whole blood was added to each tube. The tubes were capped and mixed end-over-end at 30 rpm for five minutes. Tubes were removed from the rocker and immediately placed in a quadrupole magnet (Immunicon Corp. Huntingdon Valley, Pa.) for five minutes. At the end of the magnetic separation, the sample was removed and analyzed for the presence of leukocytes using a hematology analyzer (Sysmex KX-21, Roche Diagnostic Corp.). The results (Table 6) demonstrate that selection of leukocytes with CD45-particles is dependent on particle size. The leukocyte population in whole blood is composed of three major populations: lymphocytes, monocytes and granulocytes. CD45 antigen density on the 3 leukocyte populations varies over about one order of magnitude. Further analysis revealed (FIG. 6) that the difference in selection seen with particles of different diameter correlated with antigen density.

Surprisingly, the particles of the invention select for (FIG. 6C) all 3 populations while larger particles, such as those disclosed in U.S. Pat. Nos. 5,576,185 and 6,074,884 (November 1996; Coulter, W. et al. and June 2000 Siiman, O. et al., respectively), select lymphocytes effectively but are unable to select granulocytes (FIG. 6B), which have a significantly lower CD45 antigen density than lymphocytes. With these cells, the ratio of CD45 antigen density for lymphocytes to granulocytes is 10 to 1. Accordingly, when the high to low ratio of antigen density is at least approximately 10 to 1, ferromagnetic dense particles of the invention will deplete both lymphocytes and granulocytes, but the larger particles deplete only the lymphocytes.

TABLE 6

| Particle diameter (nanometers) | Percent Selection |
| --- | --- |
| 1450 | 94 |
| 2240 | 44 |
| 3500 | 38 |

EXAMPLE 7

Large Ferromagnetic Dense Particles Preferentially Remove High Antigen Dense Cells from a Population Having a Mixture of High and Low Antigen Densities for the Same Antibody Since the ability to remove cells is dependent on antigen density and particle diameter (see EXAMPLE 6), the larger particles can be used to select for the more antigen dense targets. Within a population of cells having a range of densities for a particular antigen, it is possible to pick a particle with a diameter that permits relative removal of the high antigen density cells. For example, PC3 cells, a prostate cancer cell line available from ATCC, express Epithelial Cell Adhesion Molecule (EpCAM). Two subpopulations can be distinguished based on EpCAM antigen density. It was desirable to obtain PC3 cells that express EpCAM at a relatively low EpCAM antigen density. The starting PC3 population was made up of 25% high EpCAM density cells and 75% low EpCAM density cells having 70,000-80,000 molecules/cell for high antigen density and 15,000-20,000 molecules/cell for low antigen density, respectively. These cells were treated with particles having a diameter greater than about 2.5 microns and linked to anti-EpCAM monoclonal antibodies bound thereto. Following mixing and magnetic separation, the resultant cell subpopulation remaining in the fluid sample was composed of 98.5% low EpCAM antigen density cells (Not Illustrated).

EXAMPLE 8

Ferromagnetic Dense Particles of the Invention can be Used to Selectively Enrich Populations of Cells Used in Gene Discovery Research In order to obtain better diagnostic tools for the early detection of cancer, it is essential to determine gene profiles of cancer cells (i.e. epithelial cancer cells in circulation) and to be able to distinguish cancer cell gene profiles from normal/benign cell gene profiles. Often fluid samples (i.e. whole blood used to determine gene profiles of normal/cancer cells) are heavily contaminated with leukocytes. Thus, there is a need in the art to effectively select contaminating leukocytes without depleting cancer cells that are often present at levels one million fold lower than leukocytes. Ferromagnetic dense particle technology is particularly suited to this application because of the greater magnetic attraction properties of ferromagnetic dense particles over superparamagnetic particles, and minimal carryover of targeted cells. CD45-ferromagnetic dense particles were used to effectively select leukocyte contamination of a particular sample from 820 leukocytes/ml to 44 leukocytes/ml. In a separate experiment, epithelial cancer cells were enriched from a 7.5 ml whole blood sample from a prostate cancer patient as detected by the CellPrep/Cell Spotter System (Kagan, et al., *J. Clinical Ligand Assay*, 2002, 25:105-110). The sample had 40 prostate cancer cells/7.5 ml of blood. Following 80% leukocyte selection with CD45-ferromagnetic dense particles, the sample had 35 prostate cancer cells/7.5 ml of blood indicating that leukocyte reduction did not significantly alter the number of cancer cells (Not Illustrated).

EXAMPLE 9

Figure 7A:
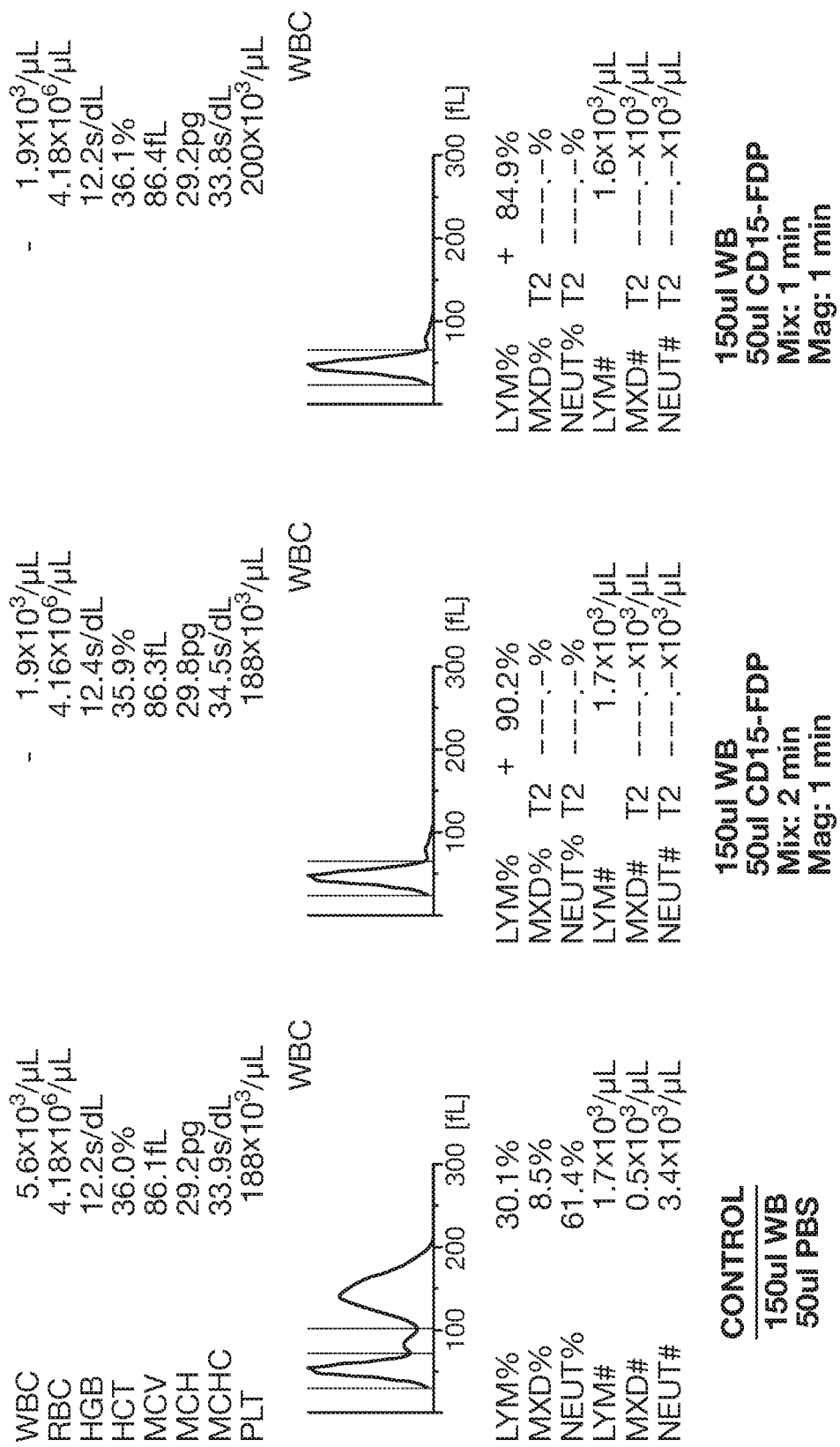
FIGS. 7A & 7B shows the effect of several mixing times on targeted granulocyte selection compared to control.
Figure 7B:
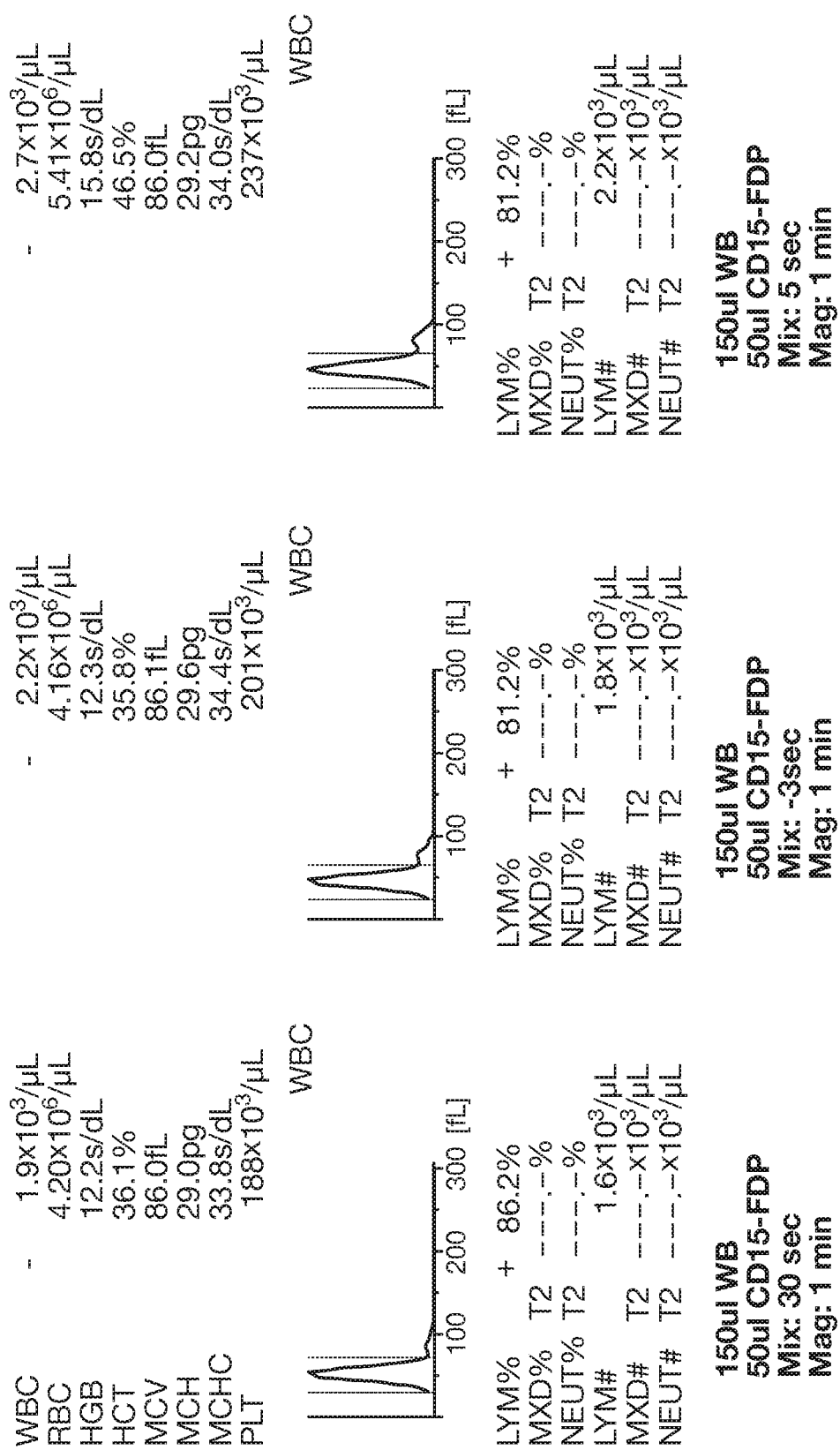

Dense Particles Complexed with CD15 Provide Very Rapid Selection of CD15 Antigen Containing Cells Whole blood was used in the selection of cells containing the antigen for CD15. 150 ul of whole blood was mixed with 50 ul of CD15-FDP for various times. After mixing by rapid vortexing or pipetting up and down, samples were placed in a magnetic field for approximately 1 min. Analysis on a hematology analyzer (Sysnex KX-21, Roche Diagnostic Corp.) showed that for mixing times around 2 seconds to around 2 minutes there was >99% selection for granulocytes containing the CD15 antigen. Such rapid selection of specific cell populations has not been shown in the art (FIGS. 7A & 7B).

EXAMPLE 10

Dense Particles of the Invention Will Separate by Gravity

Gravity, one of the two principle embodiments for particle separation, showed efficient selection for white blood cells (Table 7). Following sufficient mixing, dense particles, approximately 1 micron in diameter, were allowed to settle by gravity for (4 to 5 min). Table 7 depicts the results of this separation. While gravity separation generally takes longer than magnetic separation, both separation procedures yield equal amounts of white blood cells after selection with a negligible affect on red cell number (data not shown).

TABLE 7

|  | Whole Blood | Gravity Settled |
|---|---|---|
| White Blood Cells | $4.5 \times 10^3$ | $0.9 \times 10^3$ |
| Red Blood Cells | $3.2 \times 10^6$ | $2.94 \times 10^6$ |

While the present invention has been described in terms of its preferred embodiments, it is to be appreciated that the invention is not limited thereby, and that one skilled in the art can conceive of numerous variations and modifications of the invention as described herein, without departing from the spirit and scope of the following claims.

What is claimed is:

1. A suspension of particles for selecting a pre-determined target population of cells or cell like material or subpopulation thereof from a fluid sample comprising:
   a. a plurality of metal particles having a diameter from about 50 nanometers to a diameter of about 2.5 microns, said particles being ferromagnetic and having a density of at least 6 g/cc; and
   b. a binding agent linked to said metal particles such that said binding agent binds specifically to said target population.

2. The suspension of particles as described in claim 1, wherein said metal particles are formed from ferromagnetic metal.

3. The suspension of metal particles as described in claim 2, wherein said ferromagnetic metal is selected from the group consisting of iron, cobalt, nickel, and alloys thereof.

4. The suspension of metal particles as described in claim 2, wherein said ferromagnetic metal is nickel.

5. The suspension of metal particles as described in claim 1, wherein said diameter is from about 500 nanometers to about 1500 nanometers.

6. The suspension of metal particles as described in claim 1, wherein said diameter is from about 800 nanometers to about 1200 nanometers.

7. The suspension of metal particles as described in claim 1, wherein said density is between about 7 g/cc and about 9 g/cc.

8. The suspension of metal particles as described in claim 1, wherein said density is approximately 9 g/cc.

9. The suspension of metal particles as described in claim 1, wherein said binding agent is at least one of an antibody, drug, hormone, growth factor, lectin, enzyme and nucleic acid sequence.

10. The suspension of metal particles as described in claim 1, wherein said binding agent is an antibody that specifically binds to a cell surface antigen.

11. The suspension of metal particles as described in claim 1, wherein said binding agent is a monoclonal antibody.

12. The suspension of metal particles as described in claim 1, wherein said binding agent is biotinylated and linked to said particle through streptavidin.

* * * * *